United States Patent [19]

Ishiwata et al.

[11] Patent Number: 4,879,411

[45] Date of Patent: Nov. 7, 1989

[54] METHOD FOR RACEMIZATION OF OPTICALLY ACTIVE SERINE

[75] Inventors: Ken-ichi Ishiwata, Yokohama; Takeshi Nakamura, Zushi; Nobuyoshi Makiguchi, Fujisawa; Shoichiro Miyahara, Yokohama; Toshio Matsumoto; Kazunari Nitta, both of Oomuta, all of Japan

[73] Assignee: Mitsui Toatsu Chemicals, Inc., Tokyo, Japan

[21] Appl. No.: 219,781

[22] Filed: Jul. 18, 1988

[30] Foreign Application Priority Data

Aug. 5, 1987 [JP] Japan .................................. 62-194333

[51] Int. Cl.⁴ .............................................. C07B 55/00
[52] U.S. Cl. ..................................... 562/401; 562/567

[58] Field of Search ................................ 562/401, 567

[56] References Cited

U.S. PATENT DOCUMENTS 3,213,106  10/1965  Sasaji et al. ..................... 562/401 X Primary Examiner—Werren B. Lone
Assistant Examiner—Vera C. Clarke
Attorney, Agent, or Firm—Burns, Doane, Swecker & Mathis

[57] ABSTRACT

Optically active serine can be racemized at a high reaction rate under the relatively mild conditions by treating the optically active serine in an alkaline solution in the presence of pyridoxal phosphate or salicylaldehyde and an alkaline compound.

9 Claims, No Drawings

METHOD FOR RACEMIZATION OF OPTICALLY ACTIVE SERINE

BACKGROUND OF THE INVENTION (i) Field of the Invention

The present invention relates to a method for racemization of optically active serine. More particularly, the present invention relates to a method for racemization of serine by treating serine with an alkaline aqueous solution in the presence of pyridoxal phosphate or salicylaldehyde, and an alkaline compound.

Serine is used in the preparation of cosmetics, as a constituent of solutions for infusion and as a raw material in the preparation of antibiotics. It is also an amino acid which can be used as a raw material for the synthesis of L-tryptophan, L-tyrosine and L-cysteine. According to the specific end use, a particular isomer of serine; namely, the L-isomer, the D isomer or the racemic mixture is used. Serine obtained by proteolysis, fermentation and by enzymatic reaction is usually the L-isomer. Serine obtained by an organic synthesis is usually the racemic mixture. The demand for the L isomer, D isomer or the racemic mixture is not always equal. Therefore, it is convenient if optically active serine can be racemized, optionally in combination with optical resolution, to obtain the desired optically active isomer or so that racemic mixture can be prepared from the L-isomer or the D-isomer or their racemic mixture.

(ii) Description of the Prior Art

As methods for racemization of serine, several methods are known which are as described as follows:

(1) The method of heating optically active amino acid at a temperature of above 150° C. in a closed vessel (U.S. Pat. No. 3,213,106).

(2) The method of heating optically active amino acid at a temperature of between 105° to 150° C. and at a pH value of about 5 to 8 with m-xylene-4-sulfonic acid, ammonia and water (Japanese published Pat. No. (76) 51-41616).

(3) The method of racemization of amino acid in the presence of lower fatty acid and aliphatic or aromatic aldehyde (Japanese Laid Open Patent No. 57-12150, J. Org. Chem. 48, 843–846 (1983)).

(4) The method of racemizing serine which is conducted in the presence of cultured microorganisms, cultured strains or the extracts thereof (Japanese published Patent No. 58-52637, 58-52638, 61-4518).

(5) The method of heating optically active amino acid in the presence of strong acid or strong alkaline (Advances in Protein Chemistry 4, 339 (1948)).

(6) The method of heating optically active amino acid in the presence of pyridoxal (or pyridoxal like compound) and a metallic ion such as aluminum, iron, or copper (J. Biol. Chem, 199, 669 (1952), Bull. Chem. Soc. Jpn., 35, 1422 (1962)).

When these known methods for the racemization of optically active amino acids are applied to serine, several disadvantages have been found. More specifically, according to the methods (1), (5) or (6), the decomposition of serine dominates the racemization and as a result, the yield of DL-serine decreases. In method (2), it is necessary to use a large amount of expensive m-xylene-4-sulfonic acid as well as heating to a high temperature in the range of 105° to 150° C. In method (3), the racemization has to be done in the presence of a high concentration acetic acid and, in addition, the decomposition of the serine itself occurs. In method (4), the preparation of the microorganisms takes a long time, and in case of the existence of substances which inhibit the enzymatic reaction, this method is not applicable.

Thus, several methods for the racemization of optically active amino acid have been known, but commercial implementation of acceptable methods of achieving racemization has been difficult.

SUMMARY OF THE INVENTION

One object of the present invention is to provide a new method for racemization of optically active serine. Another object of the present invention is to provide a process which is operative industrially. To achieve these objects, the present inventors have conducted intensive research for a new method for racemization of optically active serine. Based on such research, it has been found that optically active serine can be racemized specifically when it is treated with aqueous alkaline solution in the presence of pyridoxal phosphate or salicylaldehyde and an alkaline compound.

Furthermore, under the relatively mild conditions of racemization, the method of the present invention can achieve a high reaction rate of racemization.

DETAILED DESCRIPTION OF THE INVENTION

The optically active serine used in the present invention may or may not be optically pure. That is, optically pure serine can be used as well as serine having optical purity which is decreased by contamination of enantiomers. The optically active serines are subjected to the racemization reaction in the state of an aqueous solution. There is no limitation for the concentration of the serine in the solution, but the concentration is usually from about 0.1 to about 60 wt %.

The amount of pyridoxal phosphate or salicylaldehyde used for the invention can be varied in the range of between 0.0001 to 0.1 moles per mole of optically active serine, and the optimum amount can be selected according to the conditions of racemization. More preferably, the amount is between 0.001 to 0.01 moles per mole of the optically active serine.

The alkaline compounds used in the present invention are selected from those alkaline compounds which are soluble in water. For example, ammonia, sodium hydroxide (NaOH) and potassium hydroxide can be used. From the industrial point of view, ammonia is preferred because of its high solubility in water and because it is easy to recover.

The pH value of the aqueous solution prepared by contacting the optically active serine, pyridoxal phosphate or salicylaldehyde and an alkaline compound, is adjusted to an alkaline environment, preferably above 10 and below 13. Below a pH value of 10, the reaction rate of racemization is retarded and above a pH of 13, decomposition of serine occurs.

The racemization proceeds preferably, when the racemization is conducted at a temperature of 20° to 100° C., preferably 40° to 70° C. and in a quiescent state or under low agitation.

When the temperature is below 20° C., the racemization reaction is retarded and above 100° C., the decomposition of serine occurs. As to the racemization reaction time, it depends on the temperature, the concentration of serine, the purity degree of serine and the pH value of the solution. However, it is generally completed within about a few hours to a few days.

After finishing the racemization reaction, the reacted solution is subjected to precipitation in the form of crystals by means of isoelectric point precipitation, cooling or adding alcohol, all of which are known methods. The precipitated solution is filtered and DL-serine is obtained in the form of crystals.

When ammonia is used as the alkaline compound, after finishing the racemization reaction, it is convenient to remove ammonia by means of heating the solution or introducing nitrogen gas or other stripping gas prior to the crystallization step because DL-serine can still be recovered efficiently and the removed ammonia can be collected and recycled for the next racemization reaction.

The present invention will be described more specifically by referring to the following examples and comparative examples. In the examples, yields and rates of racemization were calculated based on an analysis of the L-isomer and D-isomer measured by high performance liquid chromatography using a packet column for optically resolution (e.g., Cu-amino acid derivatives supported on silica gel which is available from Daicel Chemicals, Inc. as CHIRAL PAK WH).

The rate of the racemization reaction was calculated by the following expression based on the concentration of L-isomer and D-isomer in the reacted solution just after finishing the racemization.

Racemization rate (%) =

$$\frac{(\text{concentration of } D\text{-isomer}) \times 2}{(\text{concentration of } L\text{-isomer}) + (\text{concentration of } D\text{-isomer})} \times 100$$

When D-serine was used as the optically active serine in the racemization reaction (Example 3), the numerator of the above expression above was changed to "(concentration of L-isomer)×2".

EXAMPLE 1

60 g of L-serine was dissolved in 1,000 ml of water and 0.26 g of pyridoxal phosphate ($C_6H_{10}NO_6P \cdot H_2O$) was added. The pH value of the solution was adjusted to 13 by the addition of sodium hydroxide. The solution was agitated slowly for 48 hours at a temperature of 60° C. Then the pH value of the reaction solution was adjusted to about 5.7 by adding 35% concentration hydrogen chloride. 1,000 ml of methanol was added and the solution was agitated for 3 hours at a temperature of 10° C. The precipitated crystalline was filtered and dried. 54 g of DL-serine was obtained. The yield was 90% and the rate of racemization was 98.0%.

COMPARATIVE EXAMPLE Example 1

The procedure of Example 1 was followed except that pyridoxal phosphate was not added. The rate of racemization was 2.4%.

EXAMPLE 2

356 g of L-serine was dissolved in 644 g of water and 3 g of pyridoxal phosphate was added. The pH value of the solution was adjusted to 10.7 by adding concentrated aqua ammonia. The solution was stirred slowly for 48 hours at a temperature of 50° C. After finishing the reaction, nitrogen gas was introduced into the reaction solution and served to strip ammonia from the solution. Then the pH value was adjusted to 5.7 by adding 35% concentration hydrogen chloride. The solution was stirred for an hour at a temperature of 10° C. The precipitated crystals were filtered and washed with a small amount of cold water and the crystals were dried. 300 g of DL-serine was obtained. The yield was 84.3% and the rate of racemization was 99.8%.

COMPARATIVE EXAMPLE 2

The procedure of Example 2 was followed except that the concentrated aqua ammonia was not added. The rate of racemization was 1.8%.

EXAMPLE 3

The procedure of Example 2 was followed except that the L-serine was replaced with D-serine. 301 g of DL-serine was obtained. The yield was 84.0% and the rate of racemization was 99.9%.

EXAMPLE 4

1,000 g of L-serine was dissolved in 1,000 g of water and 4.8 g of salicylaldehyde was added. The pH value of the solution was adjusted to 11 by adding concentrated aqua ammonia. The solution was stirred slowly for 72 hours at a temperature of 50° C. After finishing the reaction, nitrogen gas was introduced into the reaction solution and ammonia was removed. The pH value was then adjusted to 5.7 by adding 35% concentration hydrogen chloride. The solution was stirred for 30 minutes at a temperature of 10° C. The precipitated crystals were filtered and washed with a small amount of cold water, and the crystals were dried. 800 g of DL-serine was obtained. The yield was 80% and the rate of racemization was 98.7%.

COMPARATIVE EXAMPLE 3

The procedure of Example 4 was followed except that salicylaldehyde was not added. The rate of racemization was 3.2%.

COMPARATIVE EXAMPLE 4

The procedure of Example 4 was followed except that the concentrated aqua ammonia was not added. The rate of racemization was 2.1%.

EXAMPLE 5 AND COMPARATIVE EXAMPLE 5

0.5 M of each amino acid (all L-isomers) shown in Table 1 were used and 2 mM of pyridoxal phosphate was added in 10 ml of water and the pH value was adjusted to 10 by adding ammonia. The solution was stirred slowly for 40 hours at a temperature of 60° C. Then, nitrogen gas was introduced in the reaction solution to remove ammonia. 1 N hydrogen chloride was added and the optical rotation was measured. The rate of racemization was calculated by the following expression based on the decrease of optical rotation.

$$\text{rate of racemization} = 1 - \frac{\text{optical rotation after the racemization}}{\text{optical rotation before the racemization}} \times 100$$

The results are shown in Table I.

TABLE I

| AMINO ACID | RATE OF RACEMIZATION (%) |
| --- | --- |
| Serine | 99.9 |
| Alanine | 6.9 |
| Valine | 2.9 |
| Leucine | 2.3 |

TABLE I-continued

| AMINO ACID | RATE OF RACEMIZATION (%) |
| --- | --- |
| Isoleucine | 0.2 |
| Threonine | 17.1 |
| Cysteine | 8.1 |
| Methionine | 1.7 |
| Glutamic Acid | 9.6 |
| Aspartic Acid | 8.6 |
| Lysine | 5.1 |
| Histidine | 0.4 |
| Phenylalanine | 10.6 |
| Tyrosine | 9.3 |
| Tryptophane | 0.6 |
| Proline | 3.4 |

It is apparent that the present invention is very effective in the racemization of serine.

What is claimed is:

1. A method for racemizing optically active serine comprising treating the optically active serine in an alkaline aqueous solution in the presence of pyridoxal phosphate or salicylaldehyde and an alkaline compound.

2. A method according to claim 1, wherein the amount of pyridoxal phosphate or salicylaldehyde present in the alkaline aqueous solution is from 0.0001 to 0.1 moles per mole of the optically active serine.

3. A method according to claim 1, wherein the optically active serine is L-serine or D-serine.

4. A method according to claim 1 wherein the alkaline compound is ammonia.

5. A method according to claim 1, wherein the alkaline compound is sodium hydroxide or potassium hydroxide.

6. A method according to claim 1, wherein the racemization is conducted at a temperature of from 20° to 100° C.

7. A method according to claim 1, wherein the racemization is conducted at a pH value of from 10 to 13.

8. A method according to claim 1, wherein the starting solution contains from 0.1 to 60% by weight of optically active serine.

9. A method according to claim 1, wherein the starting solution contains from 0.1 to 60% by weight of optically active serine, said optically active serine is L-serine or D-serine, the alkaline compound is ammonia, the reaction is conducted at a temperature of from 20° to 10020 C. at a pH value of from 10 to 13, and the ammonia is removed by heating the solution or introducing nitrogen gas into the solution.

* * * * *

UNITED STATES PATENT AND TRADEMARK OFFICE
CERTIFICATE OF CORRECTION

PATENT NO. : 4,879,411
DATED : November 7, 1989
INVENTOR(S) : Ishiwata et al

It is certified that error appears in the above-identified patent and that said Letters Patent is hereby corrected as shown below:

In claim 9, line 6, amend "10020" to -- 100° --.

Signed and Sealed this

Fifth Day of February, 1991

Attest:

HARRY F. MANBECK, JR.

*Attesting Officer*     *Commissioner of Patents and Trademarks*